United States Patent
Fujimi et al.

(10) Patent No.: US 10,470,981 B2
(45) Date of Patent: Nov. 12, 2019

(54) DENTAL CEMENT

(71) Applicant: GC Corporation, Tokyo (JP)

(72) Inventors: Atsushi Fujimi, Tokyo (JP); Syouichi Fukushima, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 15/748,710

(22) PCT Filed: Jun. 23, 2016

(86) PCT No.: PCT/JP2016/068631
§ 371 (c)(1),
(2) Date: Jan. 30, 2018

(87) PCT Pub. No.: WO2017/038218
PCT Pub. Date: Mar. 9, 2017

(65) Prior Publication Data
US 2019/0008730 A1    Jan. 10, 2019

(30) Foreign Application Priority Data

Aug. 28, 2015 (JP) ................................. 2015-168728

(51) Int. Cl.
*A61K 6/083* (2006.01)
*A61K 6/00* (2006.01)

(52) U.S. Cl.
CPC ............ *A61K 6/083* (2013.01); *A61K 6/0002* (2013.01); *A61K 6/0052* (2013.01); *A61K 6/0088* (2013.01); *A61K 6/0091* (2013.01)

(58) Field of Classification Search
USPC .................................................. 523/116, 118
See application file for complete search history.

(56) References Cited

U.S. PATENT DOCUMENTS

| | | |
|---|---|---|
| 2002/0176826 A1 | 11/2002 | Klee et al. |
| 2003/0166740 A1 | 9/2003 | Mitra et al. |
| 2007/0088096 A1 | 4/2007 | Mitra et al. |
| 2010/0240797 A1 | 9/2010 | Yarimizu et al. |
| 2011/0245368 A1 | 10/2011 | Yarimizu et al. |
| 2012/0059083 A1 | 3/2012 | Tokui et al. |

FOREIGN PATENT DOCUMENTS

| | | | |
|---|---|---|---|
| EP | 0732098 | | 9/1996 |
| EP | 1502569 | * | 2/2005 |
| JP | S51-132687 | | 11/1976 |
| JP | H11-343304 | | 12/1999 |
| JP | 2005-514490 | | 5/2005 |
| JP | 2008-088086 | | 4/2008 |
| JP | 2009-144054 | | 7/2009 |
| JP | 2010-215824 | | 9/2010 |
| JP | 2012-051856 | | 3/2012 |

OTHER PUBLICATIONS

International Search Report for PCT/JP2016/068631 dated Jul. 26, 2016.

* cited by examiner

*Primary Examiner* — Tae H Yoon
(74) *Attorney, Agent, or Firm* — IPUSA, PLLC

(57) ABSTRACT

An aspect of the present invention relates to a dental cement that includes a first agent including an organic peroxide and a (meth)acrylate; and a second agent including a thiourea derivative, an ascorbate, a vanadium compound, and a (meth)acrylate, where the first agent and the second agent each have a water content that is less than or equal to 1 mass %.

1 Claim, No Drawings

DENTAL CEMENT

CROSS-REFERENCE TO RELATED APPLICATIONS

The present application claims priority based on Japanese Patent Application 2015-168728 filed on Aug. 28, 2015, the entire contents of which are incorporated herein by reference.

TECHNICAL FIELD

The present invention relates to a dental cement.

BACKGROUND ART

In dental treatment, dental cements are used for attaching prostheses. Dental cements are also used as a protective material for treating hypersensitivity and as a sealant for children, for example.

However, dental cements have low curability under humid conditions, such as in the oral cavity, which has been a problem.

Patent Document 1 describes a polymerizable composition made up of a first component containing a (meth) acrylate and tert-butyl hydroperoxide as a peroxide; and a second component containing a (meth)acrylate, thiourea derivative as a reducing agent, and a vanadium compound as a polymerization accelerator.

Patent Document 2 describes a polymerizable composition made up of a first component containing a (meth) acrylate and cumene hydroperoxide as a peroxide; and a second component containing a (meth)acrylate, a thiourea derivative as a reducing agent, and a vanadium compound as a polymerization accelerator.

PRIOR ART DOCUMENTS

Patent Documents

Patent Document 1: Japanese Unexamined Patent Publication No. 2009-144054
Patent Document 2: Japanese Unexamined Patent Publication No. 2012-51856

SUMMARY OF THE INVENTION

Problem to be Solved by the Invention

However, there have been demands for increasing the flexural strength of the cured product.

One aspect of the present invention has been conceived in view of the foregoing problems associated with the prior art, and it is an object of the present invention to provide a dental cement that has desirable curability under humid conditions and has desirable flexural strength upon being cured.

Means for Solving the Problem

An aspect of the present invention relates to a dental cement that includes a first agent including an organic peroxide and a (meth)acrylate; and a second agent including a thiourea derivative, an ascorbate, a vanadium compound, and a (meth)acrylate, where the first agent and the second agent each have a water content that is less than or equal to 1 mass %.

Advantageous Effect of the Invention

According to an aspect of the present invention, a dental cement can be provided that has desirable curability under humid conditions and has desirable flexural strength upon being cured.

EMBODIMENTS FOR IMPLEMENTING THE INVENTION

In the following, embodiments for implementing the present invention are described.

A dental cement includes a first agent including an organic peroxide and a (meth)acrylate; and a second agent including a thiourea derivative, an ascorbate, a vanadium compound, and a (meth)acrylate. In this way, curability of the dental cement under humid conditions may be improved.

The water content of the first agent and the water content of the second agent are each less than or equal to 1 mass %, and more preferably less than or equal to 0.5 mass %. When the water content of the first agent or the water content of the second agent exceeds 1 mass %, the flexural strength of the cured product decreases.

In the present specification and the claims, a (meth) acrylate may refer to an acrylate (acrylic acid ester), a methacrylate (methacrylic acid ester), or a polymer thereof which may be an oligomer or a prepolymer including a (meth)acryloyloxy group.

Although the meth(acrylate) used in the present invention is not particularly limited, for example, methyl (meth) acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth) acrylate, 2-methoxyethyl (meth)acrylate, 2-ethoxyethyl (meth)acrylate, 2-ethylhexyl (meth)acrylate, benzyl (meth) acrylate, 2-hydroxy-1,3-bis[(meth)acryloyloxy]propane], ethylene glycol di(meth)acrylate, diethylene glycol di(meth) acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri (meth)acrylate, trimethylolethane tri(meth)acrylate, pentaerythritol tri(meth)acrylate, trimethylolmethane tri (meth)acrylate, pentaerythritol tetra(meth)acrylate, polybutylene glycol di(meth)acrylate, bisphenol A diglycidyl (meth)acrylate, or a combination of two or more of the above species may be used.

Also, a meth(acrylate) including an urethane bond may be used as the meth(acrylate).

Although the meth(acrylate) including an urethane bond is not particularly limited, for example, bis(2-(meth)acryloyloxyethyl)-2,2,4-trimethylhexamethylene dicarbamate; 1,3, 5-tris[1,3-bis{(meth)acryloyloxy}-2-propoxycarbonyl aminohexane]-1,3,5-(1H, 3H, 5H)triazine-2,4,6-trione; 2,2-bis(4-(3-(meth)acryloyloxy-2-hydroxypropyl)phenylpropane; a (meth)acrylate of an urethane oligomer of 2,2'-bis (4-hydroxycyclohexyl)propane, 2-oxepanone, hexamethylene diisocyanate, and 2-hydroxyethyl; a (meth) acrylate of an urethane oligomer of 1,3-butanediol, hexamethylene diisocyanate, and 2-hydroxyethyl (meth)acrylate, or a combination of two or more of the above species may be used.

Further, a (meth)acrylate including an acid group may be used as the (meth)acrylate.

The acid group is not particularly limited as long as it exhibits adhesive properties with respect to ceramics, such as dentin, zirconia, and alumina, and alloys containing a precious metal. For example, the acid group may be a phosphate group or a carboxyl group. A phosphate group may be particularly desirable in that it has high adhesiveness to enamel, in particular, and can effectively achieve dentin demineralization and dissolution of a smear layer of a tooth surface.

The (meth)acrylate including an acid group may include a plurality of acid groups.

Although the (meth)acrylate including a phosphate group is not particularly limited, for example, 2-(meth)acryloyloxyethyl dihydrogen phosphate; bis[2-(meth)acryloyloxyethyl] hydrogen phosphate; 2-(meth)acryloyloxyethyl phenyl hydrogen phosphate; 6-(meth)acryloyloxyhexyl dihydrogen phosphate; 6-(meth)acryloyloxyhexyl phenyl hydrogen phosphate; 10-(meth)acryloyloxydecyl dihydrogen phosphate; 1,3-bis[(meth)acryloyloxy]propane-2-dihydrogen phosphate; 1,3-bis[(meth)acryloyloxy]propane-2-phenyl hydrogen phosphate; bis[5-{2-(meth)acryloyloxyethoxycarbonyl}heptyl]hydrogen phosphate; (2-propenoic acid, 2-methyl)-phosphinicobis(oxy-2,1,3-propane); 2-(phosphonoxy)-1,3-propanediyl bismethacrylate; or a combination of two or more of the above species may be used. Particularly, 10-(meth)acryloyloxydecyl dihydrogen phosphate is desirable in view of its excellent adhesive property and stability.

Although the (meth)acrylate including a carboxyl group is not particularly limited, for example, 4-(meth)acryloxyethyltrimellitic acid; 4-(meth)acryloxyethyltrimellitic acid anhydride; 4-(meth)acryloxydecyltrimellitic acid; 4-(meth)acryloxydecyltrimellitic acid anhydride; 11-(meth)acryloyloxy-1,1-undecanedicarboxylic acid; 1,4-bis[(meth)acryloyloxy]pyromellitic acid; 2-(meth)acryloyloxyethylmaleic acid; 2-(meth)acryloyloxyethylphthalic acid; 2-(meth)acryloyloxyethylhexahydrophthalic acid; or a combination of two or more of the above species may be used. Particularly, 4-(meth)acryloxyethyltrimellitic acid and 4-(meth)acryloxyethyltrimellitic acid anhydride are desirable in view of their excellent adhesive properties.

Note that the (meth)acrylate contained in the second agent may be the same (meth)acrylate as that included in the first agent, or a different (meth)acrylate.

The content of the (meth)acrylate in the first agent may normally be from 10 to 95 mass %, and preferably from 15 to 80 mass %.

The content of the (meth)acrylate in the second agent may normally be from 10 to 95 mass %, and preferably from 15 to 80 mass %.

The organic peroxide contained in the first agent is preferably hydroperoxide in view of its stability with respect to the (meth)acrylate.

Although the hydroperoxide is not particularly limited, for example, cumene hydroperoxide, tert-butyl hydroperoxide, or a combination of two or more of the above species may be used.

The content of the organic peroxide in the first agent may normally be from 0.01 to 5 mass %, and preferably from 0.1 to 2 mass %. By arranging the content of the organic peroxide in the first agent to be greater than or equal to 0.01 mass %, the curability of the dental cement may be improved, and by arranging the content of the organic peroxide to be less than or equal to 10 mass %, storage stability of the first agent may be improved.

The thiourea derivative contained in the second agent is not particularly limited as long as it is a stable reducing substance with respect to the (meth)acrylate. For example, the thiourea derivative may be ethylene thiourea, diethyl thiourea, tetramethyl thiourea, N-acetylthiourea, N-benzoylthiourea, diphenyl thiourea, dicyclohexyl thiourea, or a combination of two or more of the above species. Particularly, N-acetylthiourea and N-benzoylthiourea are desirable.

The content of the thiourea derivative in the second agent may normally be from 0.1 to 5 mass %, and preferably from 0.1 to 1 mass %. By arranging the content of the thiourea derivative in the second agent to be greater than or equal to 0.1 mass %, the curability of the dental cement may be improved, and by arranging the content of the thiourea derivative to be less than or equal to 5 mass %, solubility with respect to the (meth)acrylate may be improved.

The ascorbate contained in the second agent is not particularly limited as long as it is a stable reducing substance with respect to the (meth)acrylate. For example, the ascorbate may be sodium ascorbate, calcium ascorbate, potassium ascorbate, a stereoisomer of these species, or a combination of two or more of the above species. Particularly, sodium ascorbate and calcium ascorbate are desirable.

The content of the ascorbate in the second agent may normally be from 0.1 to 5 mass %, and preferably from 0.1 to 1 mass %. By arranging the content of the ascorbate in the second agent to be greater than or equal to 0.1 mass %, the curability of the dental cement under humid conditions may be improved, and by arranging the content of the ascorbate to be less than or equal to 5 mass %, storage stability of the second agent may be improved.

The vanadium compound contained in the second agent is not particularly limited as long as it is a stable polymerization accelerator with respect to the (meth)acrylate. For example, the vanadium compound may be vanadium acetylacetonate, vanadyl acetylacetonate, vanadyl stearate, vanadium naphthenate, vanadium benzoyl acetonate, or a combination of two or more of the above species. Particularly, vanadium acetylacetonate and vanadyl acetylacetonate are desirable.

The content of the vanadium compound in the second agent may normally be from 0.001 to 1 mass %, and preferably from 0.01 to 0.1 mass %. By arranging the content of the vanadium compound in the second agent to be greater than or equal to 0.001 mass %, the curability of the dental cement may be improved, and by arranging the content of the vanadium compound to be less than or equal to 1 mass %, storage stability of the second agent may be improved.

The first agent and/or the second agent may further include a filler.

The filler is not particularly limited as long as it can enhance the strength of the cured product. For example, glass, such as silicic anhydride, barium glass, alumina glass, potassium glass, or fluoroaluminosilicate glass; synthetic zeolite; calcium phosphate; feldspar; fumed silica; aluminum silicate; calcium silicate; magnesium carbonate; hydrous silicic acid; hydrous calcium silicate; hydrous aluminum silicate; quartz; or a combination of two or more of the above species may be used. Particularly, silicic anhydride, fumed silica, and quartz are desirable in view of their stability with respect to the (meth)acrylate including an acid group.

Note that the filler may be surface treated with a silane coupling agent.

The coupling agent is not particularly limited as long as it is capable of coupling with the (meth)acrylate. For example, γ-methacryloyloxy propyl trimethoxysilane, vinyl trichlorosilane, vinyl triethoxysilane, vinyl trimethoxysilane, vinyl triacetoxysilane, or a combination of two or more of the above species may be used.

Also, the filler may be an organic-inorganic composite filler that is fabricated by curing a mixture of the filler and the (meth)acrylate beforehand and grinding the cured product thereafter.

Note that the filler contained in the second agent may be the same filler as that contained in the first agent or a different filler.

The content of the filler in the first agent may normally be from 4 to 90 mass %, and preferably from 15 to 80 mass %.

The content of the filler in the second agent may normally be from 4 to 90 mass %, and preferably from 15 to 80 mass %.

The first agent and/or the second agent may also contain other additives, such as a photopolymerization initiator, a stabilizer, an antimicrobial agent, and a pigment as necessary.

The photopolymerization initiator is not particularly limited, but may be 2,4,6-trimethylbenzoyl diphenylphosphine oxide, for example.

The stabilizer is not particularly limited, but may be 6-tert-butyl-2,4-xylenol, for example.

The first agent and/or the second agent is preferably a paste. In this way, operability of the dental cement may be improved.

The dental cement is used by mixing the first agent and the second agent.

The mass ratio of the first agent to the second agent when mixing the two together may normally be from 10:1 to 1:10. In this way, storage stability of the dental cement may be improved.

Although the method of mixing together the first agent and the second agent is not particularly limited, example mixing methods include an operator mixing the first and second agents manually using a spatula and mixing paper, and a method of using an auto mixing system with a mixing tip.

EXAMPLES

In the following, the present invention will be described in detail by way of Examples and Comparative Examples. However, the present invention is not limited to these examples.

Examples 1-4, Comparative Examples 1-4

Dental cements were obtained by preparing the first agent and the second agent according to the formulations [mass %] indicated in Tables 1 and 2.

TABLE 1

| | | | EXAMPLE 1 | EXAMPLE 2 | EXAMPLE 3 | EXAMPLE 4 |
|---|---|---|---|---|---|---|
| FIRST AGENT | METHACRYLATE | Bis-GMA | 10 | | 20 | |
| | | TEGDMA | 18 | 8 | | |
| | | UDMA | 20 | 40 | 20 | 40 |
| | | GDMA | | | 8 | 8 |
| | METHACRYLATE INCLUDING ACID GROUP | MDP | 3 | 3 | 3 | 3 |
| | HYDROPEROXIDE | CHP | 0.5 | 0.5 | 0.5 | |
| | | t-BHP | | | | 1 |
| | FILLER | SILICA POWDER | 45 | 45 | 45 | 45 |
| | | FUMED SILICA POWDER | 3 | 3 | 3 | 3 |
| | OTHER | IA | 0.05 | 0.05 | 0.05 | 0.05 |
| | | DISTILLED WATER | | | | |
| | | TOTAL | 100 | 100 | 100 | 100 |
| SECOND AGENT | METHACRYLATE | Bis-GMA | 10 | 8 | 8 | |
| | | TEGDMA | 5 | | | |
| | | UDMA | | | | 15 |
| | | GDMA | 15 | 20 | 22 | 15 |
| | ASCORBATE | IANa | 0.6 | | | 0.6 |
| | | LACa | | 0.4 | 0.8 | |
| | THIOUREA DERIVATIVE | NATU | | | 0.5 | |
| | | NBTU | 0.3 | 0.3 | | 0.3 |
| | VANADIUM COMPOUND | V(acac)$_2$ | 0.02 | | 0.03 | 0.02 |
| | | V(acac)$_3$ | | 0.03 | | |
| | FILLER | GLASS POWDER | 64 | 64 | 64 | 64 |
| | | FUMED SILICA POWDER | 5 | 7 | 5 | 5 |
| | OTHER | TPO | 0.1 | 0.1 | 0.1 | 0.1 |
| | | IA | 0.03 | 0.03 | 0.03 | 0.03 |
| | | TOTAL | 100 | 100 | 100 | 100 |
| | CURABILITY | NORMAL CONDITION | 5 min 00 s | 5 min 20 s | 4 min 00 s | 4 min 20 s |
| | | HUMID CONDITION | 4 min 30 s | 5 min 00 s | 3 min 40 s | 4 min 10 s |
| | | FLEXURAL STRENGTH | 112 MPa | 106 MPa | 115 MPa | 101 MPa |

TABLE 2

| | | | COMPARATIVE EXAMPLE 1 | COMPARATIVE EXAMPLE 2 | COMPARATIVE EXAMPLE 3 | COMPARATIVE EXAMPLE 4 |
|---|---|---|---|---|---|---|
| FIRST AGENT | METHACRYLATE | Bis-GMA | 30 | | | |
| | | TEGDMA | 18 | | | |
| | | UDMA | | 40 | 40 | 40 |
| | | GDMA | | 8 | 8 | 8 |
| | METHACRYLATE INCLUDING ACID GROUP | MDP | 3 | 3 | 3 | 3 |
| | HYDROPEROXIDE | CHP | 0.5 | 0.5 | | |
| | | t-BHP | | | 1 | 1 |
| | FILLER | SILICA POWDER | 45 | 45 | 45 | 40 |
| | | FUMED SILICA POWDER | 3 | 3 | 3 | 3 |
| | OTHER | IA | 0.05 | 0.05 | 0.05 | 0.05 |
| | | DISTILLED WATER | | | | 5 |
| | | TOTAL | 100 | 100 | 100 | 100 |
| SECOND AGENT | METHACRYLATE | Bis-GMA | 10 | | | |
| | | TEGDMA | | | | |
| | | UDMA | | 15 | 15 | 15 |
| | | GDMA | 20 | 15 | 15 | 15 |
| | ASCORBATE | IANa | | | | 0.6 |
| | | LACa | | | | |
| | THIOUREA DERIVATIVE | NATU | | 0.4 | | |
| | | NBTU | 0.5 | | 0.5 | 0.3 |
| | VANADIUM COMPOUND | V(acac)₂ | 0.02 | 0.03 | | 0.02 |
| | | V(acac)₃ | | | 0.03 | |
| | FILLER | GLASS POWDER | 64 | 65 | 64 | 64 |
| | | FUMED SILICA POWDER | 5 | 5 | 5 | 5 |
| | OTHER | TPO | 0.03 | 0.03 | 0.03 | 0.1 |
| | | IA | 0.03 | 0.03 | 0.03 | 0.03 |
| | | TOTAL | 100 | 100 | 100 | 100 |
| CURABILITY | | NORMAL CONDITION | 6 min 20 s | 5 min 50 s | 6 min 30 s | 4 min 20 s |
| | | | 15 min 00 s | 11 min 00 s | NOT CURED | 4 min 40 s | 4 min 10 s |
| | FLEXURAL STRENGTH | | 112 MPa | 111 MPa | 96 MPa | 79 MPa |

Note that the abbreviations in Tables 1 and 2 stand for the following substances.

IANa: Sodium isoascorbate
LACa: L(+)-calcium ascorbate
NATU: acetylthiourea
NBTU: N-benzoylthiourea
CHP: cumene hydroperoxide
t-BHP: tert-butyl hydroperoxide
V(acac)₂: vanadyl acetylacetonate sulfonate
V(acac)₃: vanadium acetylacetonate
MDP: 10-methacryloyloxydecyl dihydrogen phosphate
Bis-GMA: 2,2-bis[4-(3-methacryloyloxy-2-hydroxypropyl)phenyl] propane
UDMA: bis(2-methacryloyloxyethyl)-2,2,4-trimethylhexamethylene dicarbamate
TEGDMA: triethylene glycol dimethacrylate
GDMA: 2-hydroxy-1,3-bis(methacryloyloxy) propane
TPO: 2,4,6-trimethyl benzoyl diphenyl phosphine oxide
IA: 6-tert-butyl-2,4-xylenol
Fumed Silica Powder: Aerosil R812 (manufactured by Nippon Aerosil Co.)

(Glass Powder Fabrication Method)

Raw materials consisting of 21 mass % aluminum oxide, 44 mass % anhydrous silicic acid, 12 mass % calcium fluoride, 14 mass % calcium phosphate, and 9 mass % strontium carbonate were thoroughly mixed and then held under a temperature of 1200° C. for 5 hours using a high-temperature electric furnace to melt the mixture. Then, after cooling, the mixture was ground for 10 hours using a ball mill. Further, the ground material was passed through a 200 mesh (ASTM) sieve, to obtain a raw material powder. Then, 20 g of ethanol solution containing 10 mass % γ-methacryloyloxy propyl trimethoxysilane was added to 100 g of the raw material powder, and the materials were thoroughly mixed using a mortar. Then, the mixture was dried under a temperature of 110° C. for 2 hours using a steam dryer to obtain the glass powder.

(Silica Powder Fabrication Method)

After adding 20 g of ethanol solution containing 10 mass % vinyl triethoxysilane to silica sand powder having an average particle size of 4 μm, the materials were thoroughly mixed using a mortar. Then, the mixture was dried under a temperature of 110° C. for 2 hours using a steam dryer to obtain the silica powder.

The dental cements were used to evaluate their curability and flexural strength upon being cured.

(Curability Under Normal Condition)

The curability of dental cement under normal conditions was evaluated according to ISO 4049:2000. Specifically, the first agent and the second agent mixed together at a mass ratio of 1:1 were kneaded, and the resulting sample was filled into a polyethylene tube having an inner diameter of 4 mm and a height of 6 mm to prepare a test sample, and the temperature change of the test sample was recorded using a thermocouple to determine the cure time.

(Curability Under Humid Condition)

The curability of dental cement under humid conditions was evaluated in a manner similar to how the curability under normal conditions was evaluated, except that in kneading the first agent and the second agent, distilled water was added at 4% of the total mass of the first agent and the second agent.

(Flexural Strength of Cured Product)

The flexural strength of the cured product of dental cement was measured according to ISO 4049:2000. Specifically, the first agent and the second agent mixed together at a mass ratio of 1:1 were kneaded, and the resulting sample was filled into a 25 mm×2 mm×2 mm stainless steel mold for test sample fabrication. Then, after covering the test sample with a polyester film, a metal plate was placed and the test sample was pressurized with a clamp. Further, after replacing the metal plate with a slide glass, light was irradiated on the test sample using a LED visible light irradiator, G-Light Prima II (manufactured by GC Corporation). At this time, light was irradiated on a center portion for 10 seconds after which an irradiation window was moved to an adjacent portion overlapping with the portion that had just been irradiated by half the diameter of the irradiation window, and light was irradiated on this adjacent portion for 10 seconds. The above operations were repeated until an end portion of the test sample was irradiated with light. The operations for irradiating light were similarly performed on portions on the opposite side of the center portion. Further, the operations of irradiating light were similarly performed on the opposite face of the test sample. Then, after removing the test sample from the mold and removing burrs by polishing the test sample with a 320 grit abrasive paper, the test sample was stored in distilled water at 37° C. After 24 hours from the start of light irradiation, a load at a crosshead speed of 1 mm/min was applied and the flexural strength of the cured product was calculated.

It can be appreciated from Tables 1 and 2 that the dental cements of Examples 1-4 have desirable curability under humid conditions and have desirable flexural strength upon being cured.

In contrast, because the second agents used in the dental cements of Comparative Examples 1-3 do not contain ascorbate, their curability under humid conditions is degraded.

Further, because the first agent used in the dental cement of Comparative Example 4 contains distilled water at 4.7 mass %, the flexural strength of the cured product is reduced.

The invention claimed is:

1. A dental cement comprising:
   a first agent including an organic peroxide and a (meth) acrylate; and
   a second agent including a thiourea derivative; an ascorbate selected from among sodium ascorbate, calcium ascorbate, potassium ascorbate, and stereoisomers of sodium ascorbate, calcium ascorbate, and potassium ascorbate; a vanadium compound; and a (meth)acrylate;
   wherein the first agent and the second agent each have a water content that is less than or equal to 1 mass %,
   the first agent includes 0.1 mass % to 2 mass % of the organic peroxide,
   the second agent includes 0.1 mass % to 1 mass % of the thiourea derivative, 0.1 mass % to 1 mass % of the ascorbate, and 0.01 mass % to 0.1 mass % of the vanadium compound.

* * * * *